US00PP35204P2

(12) United States Plant Patent
Whitehouse et al.

(10) Patent No.: US PP35,204 P2
(45) Date of Patent: Jun. 6, 2023

(54) ***FRAGARIA* PLANT NAMED 'MALLING VITALITY'**

(50) Latin Name: ***Fragaria* x *ananassa***
Varietal Denomination: Malling Vitality

(71) Applicant: NIAB, Cambridge (GB)

(72) Inventors: Adam Barrie Whitehouse, Kent (GB); David William Simpson, Taunton Somerset (GB); Abigail Johnson, Kent (GB)

(73) Assignee: NIAB, Cambridge (GB)

( * ) Notice: Subject to any disclaimer, the term of this patent is extended or adjusted under 35 U.S.C. 154(b) by 0 days.

(21) Appl. No.: 17/979,163

(22) Filed: Nov. 2, 2022

Related U.S. Application Data

(60) Provisional application No. 63/276,343, filed on Nov. 5, 2021.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
See application file for complete search history.

(56) References Cited

PUBLICATIONS https://www.niab.com/malling-fruits/strawberries/malling-vitality; Retrieved from the Internet on Dec. 19, 2022. (3 pages total).*

* cited by examiner

*Primary Examiner* — Susan McCormick Ewoldt
(74) *Attorney, Agent, or Firm* — Penny J. Aguirre

(57) ABSTRACT

A new cultivar of *Fragaria* plant named 'Malling Vitality' that is characterized by its semi-upright growth habit, its large leaf size, its attitude of petiole hairs that are slightly outwards, its large sized flowers, its calyx that is smaller in relation to the corolla, its petals that are white in color, its berries that are slightly longer in relation to width, large in size, conical in shape and medium red in color with achenes that are positioned below the surface (sunken), its sepals that are held outward, its calyx diameter that is similar to the fruit diameter, and its early to medium flowering time and fruit ripening time, and its fruit bearing that is not remontant.

2 Drawing Sheets

Botanical classification: *Fragaria* x *ananassa*.
Variety denomination: 'Malling Vitality'.

BACKGROUND OF THE INVENTION

The present invention relates to a new and distinct cultivar of *Fragaria*, botanically known as *Fragaria* x *ananassa* and will be referred to hereafter by its cultivar name, 'Malling Vitality'. 'Malling Vitality' is a day neutral strawberry plant primarily adapted to the climate and growing conditions of the United Kingdom and other regions of similar climate and day length.

The new cultivar was derived from an ongoing breeding program conducted by the Inventors at a farm in Kent, United Kingdom. The goal of the breeding program was to develop a new cultivar of *Fragaria* with desirable characteristics that included fruit size, fruit shape, and disease resistance. 'Malling Vitality' arose from a controlled cross made by the Inventors in March of 2013 between an unpatented selection from the Inventor's breeding program, designated as accession number EM1795 as the female parent and an unpatented selection from the Inventor's breeding program, designated as accession number SDBL144 as the male parent. 'Malling Vitality' was selected as a single unique plant in June of 2014 from amongst the seedlings that resulted from the above cross.

Asexual propagation of the new cultivar was first accomplished by rooting stolons in Kent, United Kingdom in June of 2013. Asexual propagation by rooting of stolons and tissue culture using meristematic tissue has shown that the unique characteristics of the new cultivar are stable and reproduced true to type in successive generations.

BRIEF SUMMARY OF THE INVENTION

The following traits have been repeatedly observed and represent the characteristics of the new cultivar. These attributes in combination distinguish 'Malling Vitality' as a new and unique cultivar of *Fragaria*.

1. 'Malling Vitality' exhibits a semi-upright growth habit.
2. 'Malling Vitality' exhibits a large leaf size.
3. 'Malling Vitality' exhibits attitude of petiole hairs that are slightly outwards.
4. 'Malling Vitality' exhibits large sized flowers.
5. 'Malling Vitality' exhibits a calyx that is smaller in relation to the corolla size.
6. 'Malling Vitality' exhibits petals that are white in color.
7. 'Malling Vitality' exhibits berries that are slightly longer in relation to width.
8. 'Malling Vitality' exhibits berries that are large in size.
9. 'Malling Vitality' exhibits berries that are conical in shape.
10. 'Malling Vitality' exhibits berries that are medium red in color.
11. 'Malling Vitality' exhibits achenes that are positioned below the surface (sunken).

12. 'Malling Vitality' exhibits sepals that are held outward.
13. 'Malling Vitality' exhibits a calyx diameter that is similar to the fruit diameter.
14. 'Malling Vitality' exhibits an early to medium flowering time.
15. 'Malling Vitality' exhibits an early to medium fruit ripening time.
16. 'Malling Vitality' exhibits fruit bearing that is not remontant.

The female parent of 'Malling Vitality' differs from 'Malling Vitality' in having an earlier fruiting season and in being susceptible to powdery mildew (*Podosphaera aphanis*). The male parent of 'Malling Vitality' differs from 'Malling Vitality' in having berries that are larger in size. 'Malling Vitality' can most closely be compared to the cultivars 'Elsanta' (not patented) and 'Malling Centenary' (not patented). 'Elsanta' is similar to 'Malling Vitality' in fruit skin color. 'Elsanta' differs from 'Malling Vitality' in having fruit that is globose and irregular in shape, and a later flowering and fruiting producing season. 'Malling Centenary' is similar to 'Malling Vitality' in fruiting season. 'Malling Centenary' differs from 'Malling Vitality' in being susceptible to *Phytophthora cactorum.*

BRIEF DESCRIPTION OF THE DRAWINGS

The accompanying color photographs illustrate the overall appearance and distinct characteristics of one-year-old plants the new cultivar as grown on table-tops in coir bags under tunnels with polyethylene covers in Faversham, Kent, United Kingdom. The photographs were taken of plants that were fruiting in early July and planted in early March from a tip taken in early July the summer before and grown as a potted plant prior to planting and overwintered above 5° C.

The photograph in FIG. 1 provides a side view of 'Malling Vitality' with flowers and developing fruit.

Figure 1:
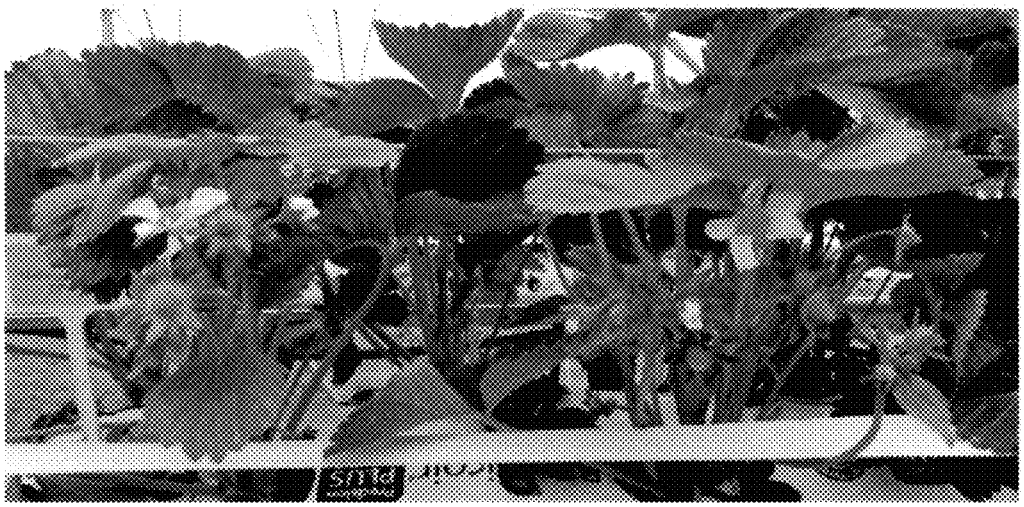
Figure 2:
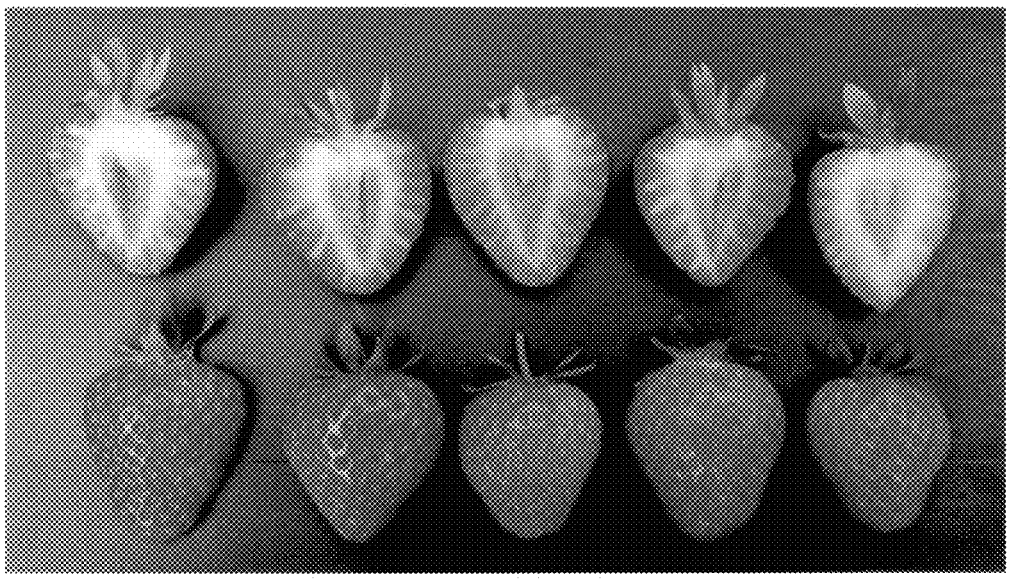

The photograph in FIG. 2 provides a close-up view of the cut fruit and whole fruit of 'Malling Vitality'.

Figure 3:
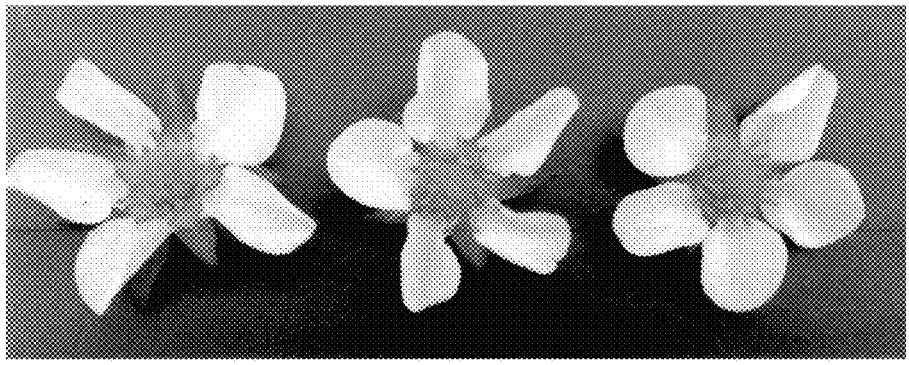

The photograph in FIG. 3 provides a close-up view of the flowers of 'Malling Vitality'.

Figure 4:
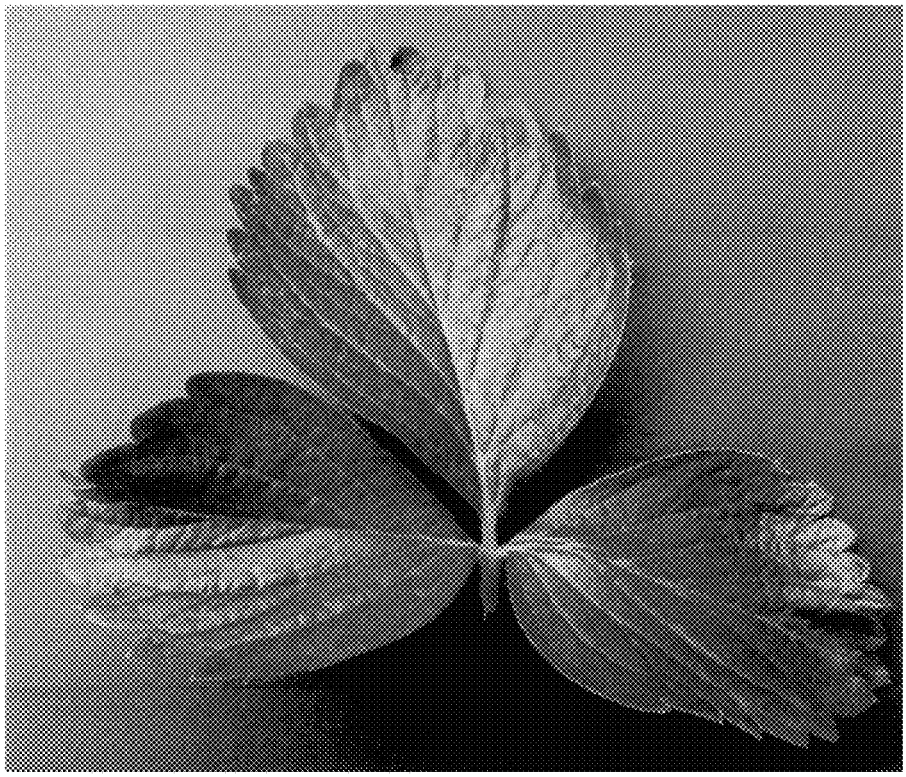

The photograph FIG. 4 provide a close-up view of a leaf of 'Malling Vitality'.

The colors in the photographs are as close as possible with digital photography techniques available, the color values cited in the detailed botanical description accurately describe the colors of the *Fragaria.*

DETAILED BOTANICAL DESCRIPTION

The following is a detailed description of one year-old plants (tip struck in June 2020 and fruited June 2021) of the new cultivar as grown outdoors on a protected table top culture in East Malling, Kent United Kingdom. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Blooming period.*—Fully flowering in May in Faversham, Kent, United Kingdom.

*Plant type.*—Herbaceous fruit producing perennial.

*Plant habit.*—Semi-upright, stoloniferous.

*Height and spread.*—Reaches about 30.1 cm in height and 34.1 cm in spread as a one-year-old plant.

*Cold hardiness.*—Not tested in areas where temperatures of less than 32° F. occur.

*Diseases and pests.*—Moderate resistance to *Phytophthora cactorum* (strawberry crown rot), no susceptibility to resistance to pests has been observed.

*Root description.*—Fibrous, 155B in color.

*Root development.*—Roots initiate in 3 to 5 days from misted tip struck under optimal conditions during active growth, a rooted young plant can be achieved within 4 weeks using method described above, subsequent growing on, including flower initiation and crown division through to dormancy will take approximately 22 to 24 weeks.

*Propagation.*—Rooting of stolons and meristem tissue culture.

*Growth rate.*—Moderately vigorous.

*Stem description.*—Acaulescent.

*Stolon description.*—Average of 16, An average of 23 cm in length and 3.4 mm in diameter, 145A, surface is sparsely covered with fine pubescent hairs; 1.3 mm in length and transparent.

Foliage description:

*Leaf division.*—Compound with three leaflets.

*Leaf arrangement.*—Basal rosettes.

*Leaf attachment.*—Petiolate.

*Leaf size.*—Average of 12.7 cm in length, 16.4 cm in width.

*Leaflet size.*—Average of 8.5 cm in length and width.

*Leaflet shape.*—Ovate.

*Leaflet margins.*—Serrate to crenate.

*Leaflet base.*—Cuneate to obtuse.

*Leaflet apex.*—Acute and rounded.

*Leaflet aspect.*—45° to 55° from vertical.

*Leaflet interveinal blistering.*—Medium.

*Leaflet venation.*—Pinnate, upper surface; N145B in color, lower surface; 145B in color.

*Leaflet surface.*—Upper surface; satiny and sparsely pubescent with soft thin hairs 1 mm in length, lower surface; matte with main veins and secondary veins moderately to densely covered with very thin soft adpressed hairs 1 mm in length, transparent and NN155D in color.

*Leaflet color.*—Upper surface 137A, lower surface 137C.

*Petiole.*—144C in color, average of 4 cm in length and 5.4 mm in width, covered with pubescent hairs, 1.8 mm in length and 155B in color.

*Petiolules.*—145B in color, average of 5.9 cm in length and 2.4 mm in width, covered with pubescent hairs 1.5 mm in length and N155B in color.

*Stipules anthocyanin coloration.*—Medium.

Flower description:

*Inflorescence.*—Compound cymose panicle.

*Inflorescence size.*—Average of 25.5 cm (base to flower tip) in length and 9.1 cm in diameter.

*Flower initiation and expression conditions.*—Temperature dependent.

*Flower longevity.*—3 to 5 days.

*Flower aspect.*—Outward to upright.

*Flower position relative to foliage.*—Upright in position relative to foliage; an average of 40° to 60°.

*Flower size.*—Average 1.13 cm in height, 3.85 cm in diameter.

*Flower buds.*—Broadly ovate to nearly orbicular in shape, at balloon shape (base of sepal to upper most tip of petal) an average of 1.22 cm in length and 1.04 cm in diameter, 155A in color.

*Flower number.*—8 (occasionally 9) per inflorescence.

*Flower fragrance.*—Present.

*Calyx.*—Average of 3.15 cm in diameter and 2.5 mm in depth.

*Sepals.*—Lanceolate in shape, an average of 10 in number per flower, an average of 10.9 mm in length and 5.4 mm in width, entire margin, 137A in color with anthocyanin absent.

*Petals.*—Average of 5, petals non-overlapping, average of 1.41 cm in length and 1.4 cm in width, apex obtuse, base attenuate, margin entire, color on both surfaces 155C.

*Peduncle.*—144A in color, an average of 18.64 cm in length and 6.9 mm in diameter, held in an upward angle facing up towards receptacle, pubescence is medium in density 1.2 mm in length and NN155B in color.

*Pedicel.*—145B in color, an average of 3.03 cm in length and 2.1 mm in diameter, held in an upwards angle, surface is densely covered with thin soft hairs 1.1 mm in length and NN155B in color.

*Bracts.*—Average of 6, narrow ovate in shape, 9.1 mm in length, 1.95 cm in width, color 146A, surface is moderately covered with thin soft hairs 1 mm in length and NN155B in color.

Reproductive organs:

*Gynoecium.*—Average of 1.5 mm in length, 0.4 mm in diameter, simple club-shaped pistils, average of 250 to 300, color; pistils 12C, stigmas 12B and receptacle 145A.

*Androecium.*—Stamens; average of 20 per flower, anther; average of 1.3 mm in length, 1 mm in width, 14A in color, pollen; 14A in color.

Fruit description:

*Shape.*—Conical.

*Surface.*—Smooth, lacking in hair, 44A in color, length in relation to width is slightly longer.

*Calyx position.*—Raised.

*Diameter of calyx relative to fruit diameter.*—Slightly smaller.

*Adherence of calyx.*—Strong.

*Glossiness.*—Strong.

*External color* (*skin*).—44A.

*Internal color* (*flesh*).—35A.

*Color of core.*—Light red.

*Fruit cavity.*—Absent or small/slight, 1.3 cm in depth.

*Evenness of color of skin.*—Slightly uneven.

*Evenness of color of flesh.*—Slightly uneven.

*Fruit sweetness/taste.*—Subjective, described as subtle sweetness with moderate acidity, average Brix 2021=8.16°.

*Fruit firmness of flesh.*—Firm.

*Fruit firmness of skin.*—Medium.

*Fruit weigh* (*secondary fruit*).—Average 20.6 grams.

*Fruit quantity.*—Average of 20.

*Fruit size.*—34.4 mm in length and 32.6 mm width.

*Season of harvest.*—Late May to June under protected table-top culture, South East UK. 2021 records (late season) 1st fruit: Jun. 14, 2021; 50% pick date: Jun. 21, 2021; last pick date Jul. 15, 2021.

*Achenes.*—Color 2A when mature, 1.7 mm in length and 0.8 mm in diameter, smooth and glabrous surface, average of 268, sunken below surface.

*Longevity of fruit.*—3 to 5 days from fully ripe and held at 4° C.

*Shipping quality.*—The variety has been included in comparative tests where it is at least as good as the standard commercial shelf-life expectancy, there has been noted fragility of skin on some tests, however typically good for 3 to 5 days.

It is claimed:

1. A new and distinct cultivar of *Fragaria* plant named 'Malling Vitality' as herein illustrated and described.

* * * * *